US00PP34506P2

(12) United States Plant Patent
Hansen

(10) Patent No.: US PP34,506 P2
(45) Date of Patent: Aug. 16, 2022

(54) ***PHLOX* PLANT NAMED 'BACKLIGHT'**

(50) Latin Name: ***Phlox paniculata* L.**
Varietal Denomination: Backlight

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 74 days.

(21) Appl. No.: 17/300,429

(22) Filed: Jun. 29, 2021

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 5/02
See application file for complete search history.

*Primary Examiner* — Kent L Bell

(57) ABSTRACT

A unique cultivar of Tall *Phlox* plant named 'Backlight' characterized by vigorous, dense, upright, multi-stemmed, winter-hardy habit with dark-green, lanceolate leaves. Flowering begins in late-July and continuing for up to five weeks in cooler weather conditions, on heavily-branched peduncles and completely cover the top of the plant in peak season. Petals are white with a pale yellow eye. The new plant shows excellent powdery mildew resistance. The new plant is especially suitable for a cut flower, for the landscape as a potted plant and in the garden as a specimen or en masse.

1 Drawing Sheet

Botanical classification: *Phlox paniculata* L.
Variety denomination: 'Backlight'.

STATEMENT REGARDING PRIOR DISCLOSURES UNDER 37 CFR 1.77(B)(6)

The first non-enabling disclosure of the claimed plant, in the form of a photograph and brief description on a website operated by Walters Gardens, Inc. on Dec. 1, 2020. The claimed plant was first sold privately by Walters Gardens, Inc. to Willoway Nurseries, Inc. on Jul. 13, 2020 followed by sales to Centerton Nursery, Inc., Prides Corner Farms and Overdevest Nurseries, LP. Walters Gardens, Inc. obtained the plant and all information relating thereto, from the inventor. No plants of *Phlox* 'Backlight' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Tall *Phlox* plant known as *Phlox* 'Backlight' and will be referred to hereafter by its cultivar name, 'Backlight', or the "new plant". The new plant was hybridized by the inventor at a wholesale perennial nursery in Zeeland, Mich. on Jul. 20, 2016 as a cross between *Phlox paniculata* 'Dick Weaver' (not patented) as the female or seed parent and the proprietary, unreleased, hybrid known by the breeder name 14-SP-PHLO-320 (not patented) as the male or pollen parent. The new plant passed initial evaluation on the spring of 2017 and was assigned the breeder code 16-46-1 through the remaining evaluation process. 'Backlight' was first asexually propagated by stem cuttings in the greenhouses at the same nursery in Zeeland, Mich. in the summer of 2017. The unique characteristics of the new plant have been found to be reproducible and stable in successive generations of asexually propagated and the resultant plants have been found to be identical to the original selection.

BRIEF SUMMARY OF THE PLANT

*Phlox* 'Backlight' is unique from all other Tall *Phlox* known to the inventor. The nearest comparison plants known to the inventor include: the female and male parents, 'Bartwentynine' U.S. Plant Pat. No. 16,259, 'Opalescence' U.S. Plant Pat. No. 33,295 and 'David' (not patented).

The female parent has purplish flowers and is much taller in habit. The male parent has flowers that are white and the foliage was lighter green.

'Bartwentynine' has a smaller, shorter habit, the flowers are more cupped and the foliage is more mildew prone. 'Opalescence' has a similar habit with flowers that are light pink with dark pink eyes. 'David' has a taller habit with smaller flower inflorescences and is more susceptible to powdery mildew.

*Phlox* 'Backlight' differs from all other *Phlox* known to the inventor in the following repeatedly observed traits in combination:

1. Vigorous plants of dense upright habit, producing tall, clean, dark-green, glabrous, lanceolate leaves;
2. Multiple lightly-branched stems produce heavily-branched panicles;
3. Flower beginning in late-July and continuing for up to five weeks, in cool conditions, completely covering plant at peak flowering;
4. Flowers are white with pale yellow eye;
5. Foliage is highly resistant to powdery mildew in conditions that would normally be exhibited on partially susceptible cultivars.

BRIEF DESCRIPTION OF THE DRAWINGS

The photographs of the new plant demonstrate the unique traits of *Phlox* 'Backlight' and the overall appearance of the plant at two-years-old growing in a full-sun display garden in Zeeland, Mich. The colors in the drawings are as accurate as reasonably possible with color reproductions. Variation in ambient light spectrum, source and direction may cause the appearance of minor variation in color.

DETAILED BOTANICAL DESCRIPTION

Figure 1:
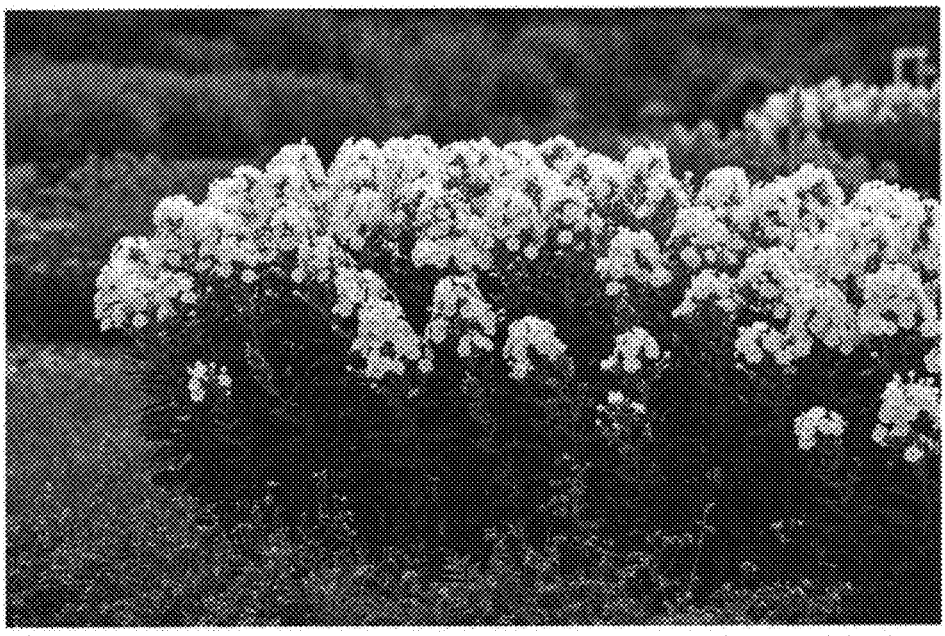
FIG. 1 shows a landscape habit view of the new plant in peak flower.
Figure 2:
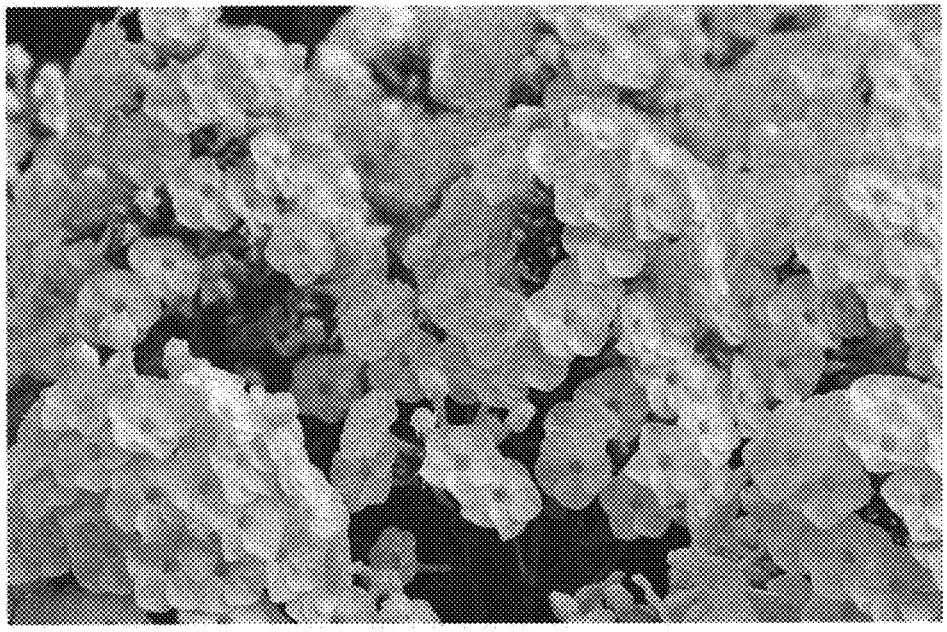
FIG. 2 shows a close-up of the flowers and buds.

The following descriptions and color references are based on the 2015 edition of The Royal Horticultural Society Colour Chart except where common dictionary terms are used. *Phlox* 'Backlight' has not been observed under all possible environments. The phenotype may vary slightly with different growing environments such as temperature, light, fertility, soil pH, moisture and maturity levels, but without any change in the genotype. The following observations and size descriptions are based on two-year-old plants in a partially shaded greenhouse or a full-sun trial garden of a wholesale perennial nursery in Zeeland, Mich. with supplemental fertilizer and water as needed.

Botanical classification: *Phlox paniculata;*

Parentage: Female or seed parent is *Phlox paniculata* 'Dick Weaver'; male or pollen parent is the proprietary hybrid known by the breeder name 14-SP-PHLO-320;

Plant habit: Winter-hardy, evergreen herbaceous perennial; dense, producing about 18 stiff, upright stems; flowering to about 77.0 cm tall and 60.0 cm wide;

Propagation: Stem cuttings; rooting in about 3 weeks;

Time to produce finished crop in 3.8 liter pots: About 8 to 10 weeks; vigorous;

Root: Fibrous and freely branching; color creamy white to tan depending on soil type;

Leaves: Simple; opposite; lanceolate; apex narrowly acute; base attenuate; margin micro-dentate; glabrous both adaxial and abaxial; to about 11.5 cm long by about 3.4 cm wide, average about 10.2 cm long and 3.2 cm wide;

Leaf color: Adaxial expanding nearest RHS 144A and abaxial expanding between RHS 145A and RHS 146D; mature adaxial between RHS 139A and RHS NN137A and mature abaxial between RHS 147B and RHS 147C; lacking anthocyanin expression;

Foliage fragrance: None detected;

Veins: Pinnate; convergent near leaf margin; glabrous adaxial and abaxial, midrib about 1.5 mm wide at base; slightly impressed adaxial and costate abaxial;

Vein color: Adaxial midrib and primary veins nearest RHS N148B; abaxial midrib nearest RHS 145C proximally, and distal midrib and primary veins nearest RHS 146D and secondary veins nearest RHS NN137B;

Petiole: Flattened; glabrous adaxial and abaxial; about 2.0 mm long and 4.0 mm wide;

Petiole color: Nearest RHS 145A adaxial and nearest RHS 146D abaxial;

Stems: Cylindrical; stiff; upright; glabrous, limited branching below flowers; to about 77.0 cm long and 9.0 mm diameter near base, average about 69 cm long and 8.0 mm diameter at base;

Stem color: Proximal portion between RHS 146C and RHS 147C with raised longitudinally striated ridges of between RHS 199D and RHS 161B; distal portion nearest RHS 146C; lacking anthocyanin expression;

Nodes: 11 nodes before flowers; average about 4.3 cm apart, greater proximally;

Node color: Color nearest RHS 146D;

Inflorescence: Upright; with 14 branched nodes; densely flowering in about the upper 26.0 cm and about 25.0 cm wide; about 600 to 900 flowers per branched stem;

Flowers: Perfect; salverform; mostly flat faced; about 24.0 mm across face and 23.0 mm long; with fused corolla tube about 22.0 mm long and 4.0 mm diameter near face and 2.0 mm diameter at base; attitude upright to outwardly;

Flower longevity: About 5 days on plant; self-cleaning;

Flower fragrance: Lightly sweet;

Buds one to two days prior to opening: Narrowly clavate to narrowly obovoid; acute apex with rounded base; petals implicate; abaxial corolla tube puberulent, bulb and calyx glabrous;

Bud size: About 19.0 mm long and 5.5 mm diameter in terminal bulb portion, and 4.0 mm diameter in corolla tube proximal bulb and base of corolla tube nearest RHS 2.5 mm diameter;

Bud color: Exposed petal bulb portion nearest RHS NN155A; corolla tube portion nearest RHS 145C; calyx nearest RHS 146B with white translucent margins nearest RHS NN155D;

Petals: Typically five, rarely six; consisting of limb and basal claw fused into corolla tube; limb obdeltoid to nearly orbicular; apex rounded, margin entire; limbs imbricate about 40 percent; limb glabrous adaxial and abaxial, adaxial corolla tube pubescent in proximal 4 to 6 mm and glabrous distally, abaxial corolla tube puberulent; with no anthocyanins;

Petal size: Limb about 10.0 mm long and 12.0 mm wide near middle; tube about 22.0 mm long and 4.0 mm diameter near face and 3.0 mm diameter near base;

Petal color upon first opening:

*Adaxial.*—Limb nearest RHS NN155D, with center eye between RHS 2D and RHS NN155D; distal 12.0 mm of corolla tube between RHS 2D and RHS NN155D, proximal 10.0 mm of corolla tube portion nearest RHS 145D.

*Abaxial.*—Limb nearest RHS NN155D, corolla tube between RHS 145C and RHS 150D.

Petal color upon maturity:

*Adaxial.*—Limb nearest RHS NN155D, with center eye between RHS 2D and RHS NN155D; distal 12.0 mm of corolla tube between RHS 2D and RHS NN155D, proximal 10.0 mm of corolla tube portion nearest RHS 145D.

*Abaxial.*—Limb nearest RHS NN155D, corolla tube between RHS 145C and RHS 150D.

Androecium: Typically five;

*Filaments.*—Typically five, adnate to inner corolla to various heights about 12.0 mm to 17.0 mm from base; free in the distal 0.5 mm and 0.2 mm in diameter; color nearest RHS 150D.

*Anther.*—Five; oblong ellipsoidal; basifixed; longitudinal; about 4.0 mm long by 1.0 mm wide; color nearest RHS 11D.

*Pollen.*—Nearly microscopic; color nearest RHS 18C.

Gynoecium: One pistil per flower; 20.5 mm long;

*Style.*—Cylindrical; about 17.0 mm long and 0.3 mm diameter when flower is mature; persistent after flower abscission; color nearest RHS 145C.

*Stigma.*—Typically trifid in proximal 1.0 mm long; about 0.3 mm diameter; color nearest RHS 11C.

*Ovary*.—Inferior; turbinate; glabrous; lustrous; acute apex and truncate base; about 2.5 mm long and 1.2 mm diameter at base; color nearest RHS 146B.

Calyx: Campanulate; about 6.0 mm long and 3.0 mm across at apex;

Sepals: Typically five, rarely six; linear; adaxial slightly lustrous and matte abaxial; narrowly acute apex, fused in basal 4.0 mm, free in distal 3.0 mm; margin entire; individually about 7.0 mm long and 1.5 mm wide at fusion;

Sepal color: Adaxial between RHS 146B and RHS 141A with transparent to translucent margin about 0.5 mm wide; abaxial between RHS 146B and RHS 141A with a transparent to translucent margin; margin adaxial and abaxial nearest RHS NN155D; no anthocyanin;

Peduncle: Glabrous; stiff; upright; cylindrical; highly branched; to 26.0 cm long and 5.0 mm diameter; with up to 14 branches at about a 50 degree angle above horizontal, branches to about 2.5 mm diameter at base and 18.0 cm long;

Peduncle color: Nearest RHS 146C;

Pedicel: Cylindrical; glabrous; flexible; upright to outwardly; to about 3.0 mm long and 0.7 mm diameter;

Pedicel color: Between RHS 138A and RHS 146D;

Fruit: Dehiscent, few-seeded capsule, typically 1 seed; fecundity low; flattened ellipsoidal; glabrous; to about 4.5 mm long and 2.5 mm diameter in middle; color at maturity nearest RHS N200A;

Seeds: Flattened ellipsoidal; glabrous; to 5.0 mm long, 3.0 mm across and 1.5 mm thick; color nearest RHS 202A;

Hardiness and culture: The new plant grows best with full sun, light moisture and deep drainage; hardy to at least from USDA zone 3 through 8.

Disease and pest resistance: *Phlox* 'Backlight' demonstrates excellent powdery mildew (*Erysiphe cichoracearum*) resistance under conditions that would normally show symptoms. No nest resistance beyond that common for *Phlox* has been observed.

I claim:

1. A new and distinct cultivar of Tall *Phlox, Phlox* plant named 'Backlight', as herein described and illustrated.

* * * * *